(12) United States Patent
Bytton

(10) Patent No.: US 11,648,283 B2
(45) Date of Patent: May 16, 2023

(54) **HIGH YIELD EXTRACTION METHOD FOR AND PRODUCTS OF *CORYDALIS* PLANTS**

(71) Applicant: PLANT SYNERGY INC., Yorklyn, DE (US)

(72) Inventor: Armand Bytton, Pasadena, CA (US)

(73) Assignee: PLANT SYNERGY INC., Yorklyn, DE (US)

( * ) Notice: Subject to any disclaimer, the term of this patent is extended or adjusted under 35 U.S.C. 154(b) by 0 days.

(21) Appl. No.: 17/587,827

(22) Filed: Jan. 28, 2022

(65) Prior Publication Data

US 2022/0143118 A1    May 12, 2022

Related U.S. Application Data

(60) Continuation-in-part of application No. 17/093,937, filed on Nov. 10, 2020, which is a division of application No. 16/668,474, filed on Oct. 30, 2019, now Pat. No. 10,864,239.

(51) Int. Cl.
| | |
|---|---|
| *A61K 36/185* | (2006.01) |
| *A61K 31/05* | (2006.01) |
| *A61K 31/404* | (2006.01) |

(52) U.S. Cl.
CPC ............ *A61K 36/185* (2013.01); *A61K 31/05* (2013.01); *A61K 31/404* (2013.01); *A61K 2236/333* (2013.01); *A61K 2236/39* (2013.01)

(58) Field of Classification Search
CPC .................................................. A61K 36/185
See application file for complete search history.

(56) References Cited

U.S. PATENT DOCUMENTS

| | | |
|---|---|---|
| 5,242,926 A | 9/1993 | Hsieh et al. |
| 2013/0344175 A1 | 12/2013 | Chen et al. |
| 2020/0253264 A1 | 8/2020 | Rousseau et al. |
| 2020/0323936 A1 | 10/2020 | Mirzatuny |
| 2021/0038560 A1 | 2/2021 | Holzer et al. |

FOREIGN PATENT DOCUMENTS

| | | |
|---|---|---|
| WO | 2014134254 A1 | 9/2014 |
| WO | 2020136627 A1 | 7/2020 |

OTHER PUBLICATIONS

Ou et al. Journal of Chromatography A, 2006, 1117(2): 163-169.*
Wang et al., RSC Advance, 2017, 7(84): 53545-53551.*
Denisenko et al. CAS: 116: 170156, 1991.*
Wang et al. "Applying target data screening followed by characteristic fragment filtering for the comprehensive screening and identification of alkaloids in Corydalis yanhusuo W. T. Wang by UPLC-Q-TOF/MS" RSC Advances, vol. 7 (Nov. 21, 2017).
Ding et al. "Qualitative and quantitative determination often alkaloids in traditional Chinese medicine Corydalis yanhusuo W.T. Wang by LC?MS/MS and LC?DAD" Journal of Pharmaceutical and Biomedical Analysis, vol. 45 (Jun. 14, 2007) pp. 219-226.
Wan et al. "Alkaloid extract of Corydalis yanhusuo inhibits angiogenesis via targeting vascular endothelial growth factor receptor signaling" BMC Complementary and Alternative Medicine, . vol. 18 Article 359 (2019) pp. 1-13.
Corydalis, CBD, and Pain Response Green Earth Medicinals (Aug. 20, 2019).
PCT International Search Report and Written Opinion, PCT/US22/14372, dated Apr. 13, 2022.
Canadian Intellectual Property Office, Application No. 3,157,816, PCT No. US2019058771, Plant Synergy Inc. Jul. 13, 2022.

* cited by examiner

*Primary Examiner* — Rei Tsang Shiao
(74) *Attorney, Agent, or Firm* — Flener IP & Business Law; Zareefa B. Flener

(57) ABSTRACT

A method of extracting a *C. yanhusuo* plant comprising the steps of harvesting and drying the plant; extracting the alkaloids from the plant in a solvent; filtering the solvent—*C. yanhusuo* plant mixture to remove the solvent and extracted alkaloids from a spent plant matter; drying the spent plant matter; purifying and separating the extracted alkaloids from the solvent; and mixing the purified alkaloids back into the dried spent plant matter. Also, products of the method include vaporizing liquids, medicinal compositions, kief compositions, rolling papers, and filters for tobacco and vaporizing equipment comprising the mixture of the purified alkaloids and the dried spent plant matter produced according to the method. Further, a *C. yanhusuo* plant having a total alkaloid content of about 3%, of which 97% of the total alkaloid content is bulbocapnine and tetrahydropalmatine (THP).

20 Claims, 4 Drawing Sheets

Bulcocapnine

*l* - THP

HIGH YIELD EXTRACTION METHOD FOR AND PRODUCTS OF *CORYDALIS* PLANTS

CROSS-REFERENCE TO RELATED APPLICATIONS

The present application is a Continuation-in-Part of U.S. application Ser. No. 17/093,937, filed Nov. 10, 2020, which is incorporated herein by reference in its entirety.

FIELD OF THE INVENTION

The present invention relates to methods of high yield extraction of herbaceous plant matter. More particularly, the present invention relates to methods of high yield extraction of *Corydalis yanhusuo* plant species and products thereof for medicinal and commercial use, as well as use in combination with extracts of cannabis.

BACKGROUND

The historically therapeutic plant *Corydalis yanhusuo*, is indigenous to high altitude grasslands of China. There are at least 470 species of the genus *Corydalis*, with *Corydalis yanhusuo* (also referred to herein as *C. yanhusuo*) being known to traditional Chinese medicine as an important therapeutic medicine. The tuber of the plant is often processed using a combination of drying, grinding, or fermenting to yield a product which is consumed as an analgesic, at least in traditional Chinese medicine.

Crude plant extracts or plant material traditionally consumed by ingestion contains many compounds, such as secondary metabolites, which may affect many targets in the body simultaneously. These complex mixtures of phytochemicals may have numerous, synergistic effects in the body and "minor" metabolites may likely affect targets that have an equilibrizing effect that can, for example, mitigate side effects as compared to a synthetic pure pharmaceutical. The overall effect may be more desirable and more potent than that of only one compound alone.

Known cultivars of the cannabis plant produce hundreds of compounds with their own therapeutic potential and the capability to induce synergic responses when combined. This heightened effect is referred to as the "entourage effect". Often the entourage effect of the supportive but undescribed molecules in a whole plant extract may potentiate the target molecules, yielding a more desirable result. For instance, one study tested the anti-tumor efficacy of the botanical drug preparation (whole plant extract) versus pure tetrahydrocannabinol (THC) against breast cancer. <URL: https://www.sciencedirect.com/science/article/abs/pii/S0006295218302387>. The results provide that while pure THC acted by activating cannabinoid $CB_2$ receptors and generating reactive oxygen species, the whole plant extract modulated different targets and mechanisms of action. These, and other similar experimental results suggest that standardized cannabis drug preparations, rather than pure cannabinoids, could be considered as part of the therapeutic armamentarium to manage various diseases and in this particular study, breast cancer.

However, processes for extraction of the alkaloids related to how they influence the entourage effect are under advanced and not available for the scientific and global community.

The alkaloids contained in *Corydalis yanhusuo* are believed to possess significant bioactivity and at least include bulbocapnine, tetrahydropalmatine (THP), in addition to protopine, α-allocryptopine, tetrahydrocolumbamine, coptisine, palmatine, berberine, dhydrocorydaline, tetrahydroberberine, corydaline, and tetrahydrocoptisine.

Plant hybridization of plant species, such as those in the *Corydalis* genus, may occur naturally and through cultivation. Hybridized medicinal or non-medicinal plants provide many benefits, including phytochemical and phytonutrient enriched properties and increased yields of certain alkaloids that have yet to be further researched and discovered. Such plants may be desirable in embodiments of the present extraction method for the unique outputs and thus compositions achievable.

Two receptors, CB1 and CB2, of the endocannabinoid system have been identified so far, with consensus being that there very well could be more yet to be discovered. CB1 and CB2 receptors are both G-protein coupled receptors. Endocannabinoids act as retrograde signaling messengers that stimulate presynaptic CB1 receptors on neurons in the brain. This stimulation results in regulation of ion channel activities, inhibition of adenylate cyclase activity and activation of the mitogen-activated protein kinase cascade.

CB1 receptors are the most abundant receptors in the mammalian brain, and also have been detected in other peripheral tissues and cells such as testis, eye, urinary bladder, ileum and adipocytes, though in lower concentrations than in the brain. CB1 receptors are found in brain areas related to the control of anxiety and emotional perception. In rats, CB1 receptors have been found with 5-HT transporters in the amygdale, suggesting that they mediate 5-HT release therefore possibly a target for the treatment of disorders related to mood, anxiety and cognition.

*Corydalis* species (e.g. *Corydalis yanhusuo*) have been shown to display potent CB1 receptor binding. The mood enhancing and stimulant properties of the whole plant extract of *Corydalis yanhusuo* has been traditionally utilized by the people of China. In addition to these effects, preparations of *C. yanhusuo* has shown it can mitigate pain. These effects have been confirmed by proving serotonin-uptake inhibition activity with unfermented alkaloid extracts proving to possess a higher activity to bind CB1 receptor compared to that of fermented alkaloid extracts.

Despite the vast forward progress in herbal medicinal research, the properties (specific phytonutrients, phytomaterials, and certain phytochemicals) and effects of the alkaloids extracted from plant species of *Corydalis yanhusuo* and current extraction processes to advance these properties and effects regarding how they affect the biochemical reactions of the endocannabinoid system remain in need of further development.

BRIEF SUMMARY OF THE INVENTION

A method of extracting a *C. yanhusuo* plant which includes the steps of harvesting and drying the *C. yanhusuo* plant; extracting the alkaloids from the *C. yanhusuo* plant in a solvent; filtering the solvent/*C. yanhusuo* plant mixture to remove the solvent and extracted alkaloids from a spent *C. yanhusuo* plant matter; drying the spent *C. yanhusuo* plant matter; purifying and separating the extracted alkaloids from the solvent; and mixing the purified alkaloids back into the dried spent *C. yanhusuo* plant matter.

Also provided is a vaporizing liquid having a mixture of the purified alkaloids and the dried spent *C. yanhusuo* plant matter produced according to the method of extraction. Further provided is a vaporizing liquid wherein the extraction method further has a step of solubilizing in a second solvent.

Further provided is a medicinal composition having a mixture of the purified alkaloids and dried spent *C. yanhusuo* plant matter produced according to the method of extraction.

Moreover, a kief composition is provided having a mixture of the purified alkaloids and dried spent *C. yanhusuo* plant matter produced according to the method of extraction.

Even further provided are papers for combustion, for instance in smoking, impregnated or coated with a mixture of the purified alkaloids and dried spent *C. yanhusuo* plant matter produced according to the method of extraction.

A *C. yanhusuo* plant having a total alkaloid content of 3%, of which 97% of the total alkaloid content is bulbocapnine and tetrahydropalmatine (THP).

Also provided are filters, for example for smoking or vaporization equipment, containing, impregnated or coated with, a mixture of the purified alkaloids and dried spent *C. yanhusuo* plant matter produced according to the method of extraction.

Numerous other features and advantages of the present invention will be readily apparent to those of ordinary skill in the art upon reading of the following detailed description of presently preferred, but nonetheless illustrative, embodiments of the present invention when taken in conjunction with the accompanying figures. In this respect, before explaining embodiments of the invention in detail, it is to be understood that the invention is not limited in its application to the details of construction and to the arrangements of the components set forth in the following description or illustrated in the figures. The invention is capable of other embodiments and of being practiced and carried out in various ways. Also, it is to be understood that the phraseology and terminology employed herein are for the purpose of description and should not be regarded as limiting.

Before undertaking the detailed description of the invention below, it may be advantageous to set forth definitions of certain words and phrases used throughout this patent document. Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Those skilled in the art will appreciate that the invention described herein is susceptible to variations and modifications other than those specifically described. It is to be understood that the invention includes all such variations and modification which fall within its spirit and scope.

BRIEF DESCRIPTION OF THE FIGURES (NON-LIMITING EMBODIMENTS OF THE DISCLOSURE)

The invention will be better understood and aspects other than those set forth above will become apparent when consideration is given to the following description thereof. Such description makes reference to the annexed figures, wherein.

DETAILED DESCRIPTION

Figure 1:
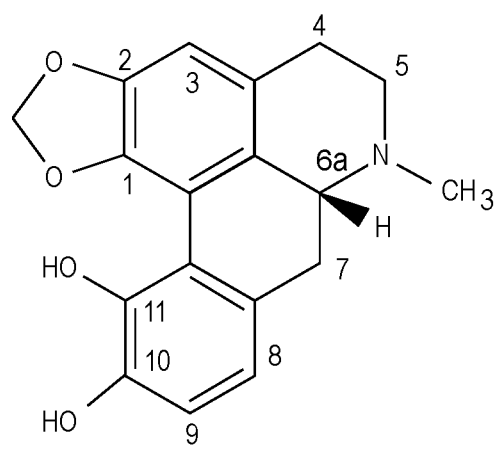
FIG. 1 illustrates a bonding diagram of Bulbocapnine and tetrahydropalmatine.
Figure 1:
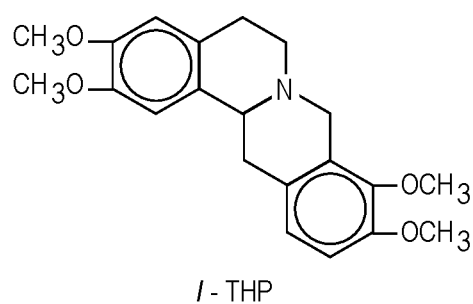

Hereinafter, methods of high yield extraction of plant matter of a *Corydalis yanhusuo* plant species and products thereof for medicinal and commercial use have been described.

An embodiment of the invention is a method of extracting a *C. yanhusuo* plant including the steps of harvesting and drying the plant; extracting the alkaloids from the plant in a solvent; filtering the solvent—*C. yanhusuo* plant mixture to remove the solvent and extracted alkaloids from a spent *C. yanhusuo* plant matter; drying the spent plant matter; purifying and separating the extracted alkaloids from the solvent; and mixing the purified alkaloids back into the dried spent plant matter.

Following the completion of the harvesting and drying of the *C. yanhusuo* plant, the *C. yanhusuo* plant is combined with a known solvent (the solvent may be determined upon the method of 'separation' chosen and the criteria of the equipment being used). During this step in the process, the bulk of the desired phytochemicals soluble in the selected solvent are isolated away from bulk fibers, structural plant material and cell debris. Depleted waste materials such as fibers, structural plant components, and cell debris may be disposed of in chemical waste containers. In an alternate embodiment of the invention, other phytochemicals, phytonutrients, or phytomaterials such as cannabidiols (CBD) may be added to the plant and the solvent during this extraction step and in another embodiment, could be mixed at the end of the process. Again, in other embodiments, other cannabis components could be added such as, for instance, but not limited to, cannabielsoin (CBE), cannabinol (CBN), cannabichromene (CBC), and cannabigerol (CBG), thus leading to different ultimate combinations.

This mixture may be prepared in a simple base extract and processed by Soxhlet extraction or other industry accepted methodologies or systems. In the example of using Soxhlet extraction, the solvent is then removed, and the extract is subjected to acidification ($H_2SO_4$). An organic solvent (such as hexane) is used to wash the acidic solvent solution and the organic phase discarded, followed by adding an ammonia solution to neutralize it and result in an alkaline solution. This alkaline solution may be further extracted with dichloromethane.

These solvent fractions can then be collected into a flask, filtered, and the solvent removed to yield a liquid containing only the desired alkaloids. Removal of the solvent from the desired alkaloids may be carried out by known processes, including, but not limited to, distillation, open-dish evaporation, reduced-pressure evaporation, rotary evaporation, vacuum, lyophilization, or a combination of methods thereof. For instance, removal of the solvent in one embodiment is by rotary evaporation.

The solvent may be a known food grade solvent, including but not limited to ethanol, methanol, hydroalcohol, acetone, acetonitrile, hexane, heptane, hexane, chloroform, dichloromethane, water, and mixtures thereof. For instance, in one embodiment, the solvent is ethanol. In an embodiment of the method, the amount of solvent added is about 1:1 with the plant matter.

Solvents are chosen based on equipment specifications and the relative covalency of the compounds. There are many covalent compounds which could be used in this method. The heating step has particular temperature and time parameters dictated by the equipment used. For instance, ethanol, which is used in one embodiment, evaporates very easily under low vacuum, and thus the equipment cycling parameters are chosen based on the need for evaporation of the ethanol solvent.

Removal of the solvent can be, but is not limited to, a process selected from distillation, open-dish evaporation, reduced-pressure evaporation, rotary evaporation, vacuum, lyophilization, or a combination of methods thereof. In one embodiment, the solvent is removed by rotary evaporation which is efficient in removing the solvent.

After filtration, the remaining alkaloid extracts that were removed from the solvent are then subjected to the purification and separation techniques to isolate the target alkaloid molecules away from the myriad of other phytochemicals extracted by the solvent, which may not be desired. The purification and separation of the alkaloids in the method is carried out by passing the solvent and extracted alkaloids over or through a process selected from column chromatography comprising a reverse stationary phase, a normal stationary phase or combination thereof, ion-exchange chromatography, gel-permeation (molecular sieve) chromatography, affinity chromatography, paper chromatography, thin-layer chromatography, gas chromatography, dye-ligand chromatography, hydrophobic interaction chromatography, pseudoaffinity chromatography, and high-pressure liquid chromatography (HPLC). Use of a particular purification and separation technique is dictated by the equipment design to use the modality.

An example of an undesired product of herbal plant extraction are oxalates, which are found in raw plant material of C. yanhusuo. Traditional and contemporary methods of preparation serve to reduce levels of potentially harmful oxalates found in C. yanhusuo. Known analyses have indicated levels of 3.6-5.1% oxalate in wild type plants, which falls within the median range for crop plants like spinach or kale. It has been previously speculated that physical crushing of the plant and the fermentation process reduce the potentially harmful effects of oxalic acid. In particular, free oxalic acid is likely to complex with cell wall-associated calcium salts and precipitate as calcium oxalate when plant material is crushed. Purification and separation techniques (such as flash chromatography) should enable maximum removal of oxalates as they should remain outside of the established absorption medium through these methods. The eluents containing the target alkaloids at higher yields are collected for further processing.

Once the active target molecules are purified to an acceptable extent and concentrated, the isolated alkaloid products are then washed, filtered and dried. The purified, concentrated products (bulbocapnine, THP, and other target alkaloids or optionally added phytochemicals) are re-combined with the dried spent plant matter to produce an optimized product, a "whole herb," to take advantage of the target alkaloids potency while utilizing the heightened "entourage effect" of the many undescribed phytochemicals found in the dried spent plant matter.

This mixture of the purified alkaloids combined with the dried spent plant matter can then be "sprinkled" on other herbal products (i.e., ginger, turmeric, holy basil, among other known products) or mixed with other phytochemicals, phytonutrients, or phytomaterials by the consumer, packed into capsules or tablets, or re-solubilized into a second solvent liquid for further formulation, medicinal or commercial uses including application on or in known delivery vehicles, such as vaporizing liquids, electronic liquids (e-liquids) for vaporization, medicinal compositions, kief, saturated or infused rolling papers, and filters for tobacco and vaporizing equipment, and internasal delivery systems such as a spray.

In one embodiment, the process of separation and isolation of alkaloids from Corydalis species via flash chromatography can be carried out after filtration. Referencing relevant alkaloid reference standards in order to properly identify the target molecules we use a Biotage Flash chromatography Isolera Single Channel system or Biotage Selekt Flash Chromatography system utilizing a C18 reverse phase silica column and detected at a UV wavelength of 254 nm. Some solvents used may be Dichloromethane, acetone, methanol and acetonitrile. Methanol and 1% acetic acid or formic acid in water mixed over a 10 minute gradient program, passes through the C18 column, separating out our target products by detectable peaks on the chromatogram. Following the separation of components by flash chromatography, collected eluents are then filtered and processed again through the Flash Chromatography unit (Biotage Isolera or Selekt chromatography system), utilizing resins with different characteristics such as charge or hydrophobicity yielding pure target products of bulbocapnine, protopine, α-allocryptopine, tetrahydrocolumbamine, coptisine, palmatine, berberine, dehydrocorydaline, D,L-tetrahydropalmatine, tetrahydroberberine, corydaline and tetrahydrocoptisine (as well as others). These concentrated molecules can then be re-suspended into the whole herb extract to produce the desired product at multiple units of concentration.

The method could also further include solubilizing the mixture of the purified alkaloids and the dried spent plant matter in a second solvent, such as, for instance an electronic vaporizer liquid ("e-liquid") or in a second solvent before putting in an e-liquid. The second solvent could be a known food grade solvent, including but not limited to ethanol, methanol, hydroalcohol, acetone, acetonitrile, hexane, heptane, hexane, chloroform, dichloromethane, water, and mixtures thereof.

The second solvent liquid may be the same or different from the solvent of the mixture of the plant before the purification and separation step of the method. In one embodiment of the method, the amount of second solvent liquid added is about 1:1 of the mixture of the purified alkaloids and dried spent plant matter product.

Either the plant and the solvent mixture during extraction or the final mixture of the purified alkaloids and the dried spent plant matter can be mixed with other herbal products, including ginger, turmeric, holy basil, and cannabidiols (CBD) from known cannabinoids.

In an embodiment of this invention, cannabidiols (CBD) could be added to the plant and the solvent during extraction, and in another embodiment, CBD can be added at the end of the process after all products are dried/mixed together. In yet another embodiment, a different cannabis component can be used in the mix such as, for instance, but not limited to, cannabielsoin (CBE), cannabinol (CBN), cannabichromene (CBC), cannabigerol (CBG) and mixtures thereof. The cannabidiol source can be selected from, but is not limited to, hemp plant, crude hemp oil, kief, nabiximol, epidiolex, and combinations thereof, and preferably is crude hemp oil.

Cannabinoids can be defined as any extract, isolate, or derivative of the Cannabaceae genus of botanicals, comprising the C. sativa, C. indica, and C. ruderalis families, or any combination thereof, produced by—or as part of—a synthetic transformative process involving any other combination of cannabinoids or their derivatives. This starting material can be obtained from any commercially available sources, or synthesized in situ, at a time prior to inception of the methods described herein. The cannabidiol (CBD) sources can include but are not limited to hemp plant, crude hemp oil, nabiximol, epidiolex, and combinations thereof to provide the cannabidiols (CBD) for combination with the mixtures in the present methods. In one embodiment of the cannabidiol (CBD) is crude hemp oil. In an alternative embodiment, a combination of cannabidiols is utilized in the methods presented herein.

Provided in FIG. 1 is a bonding diagram of bulbocapnine and tetrahydropalmatine. By the present method, alkaloids such as bulbocapnine and tetrahydropalmatine and some minor alkaloids such as protopine, α-allocryptopine, tetrahydrocolumbamine, coptisine, palmatine, berberine, dehydrocorydaline, tetrahydroberberine, corydaline and tetrahydrocoptisine are isolated, concentrated, and re-suspended with the raw whole C. yanhusuo plant matter of the method in order to provide a full-Spectrum extract with concentrated, stabilized target molecules.

The process of separation and isolation of alkaloids from C. yanhusuo species via flash chromatography can be carried out after filtration. Referencing relevant alkaloid reference standards in order to properly identify the target molecules, a Biotage® Flash chromatography Isolera Single Channel system or Biotage Selekt® Flash Chromatography system utilizing a C18 reverse phase silica column and detected at a UV wavelength of 228 nm was used. Methanol and 1% acetic acid in water mixed over a 25-minute gradient program, passes through the C18 column, separating out the target alkaloids by detectable peaks on the chromatogram. This is a typical HPLC chromatogram of a methanol extract and the retention times of major compounds purported to elute at 2.38, 3.15, 4.89 and 7.84 and a flow rate of 1 ml/min.

Following the separation of components by flash chromatography, collected eluents are then filtered and processed again through the Flash Chromatography unit (Biotage Isolera or Selekt chromatography system), utilizing resins with different characteristics such as charge or hydrophobicity yielding pure target products of bulbocapnine and tetrahydropalmatine (THP), at a minimum concentration of 50% of total alkaloids, in addition to a minimum of doubling the concentration of other target molecules such as protopine, α-allocryptopine, tetrahydrocolumbamine, coptisine, palmatine, berberine, dehydrocorydaline, tetrahydroberberine, corydaline and tetrahydrocoptisine. These concentrated molecules were then re-suspended into the whole herb extract to produce the desired product at multiple units of concentration.

In one embodiment, at the extraction phase, a concentration of approximately 20-30% bulbocapnine and tetrahydropalmatine (THP) is expected, constituent to a total alkaloid content of approximately 70-90%. After the chromatography steps, the target molecules bulbocapnine and tetrahydropalmatine (THP) should have a minimum concentration of 50% total alkaloid content. Other non-primary target molecules including protopine, α-allocryptopine, tetrahydrocolumbamine, coptisine, palmatine, berberine, dehydrocorydaline, D,L-tetrahydropalmatine, tetrahydroberberine, corydaline and tetrahydrocoptisine have a minimum concentration range from 2:1, 5:1, 8:1, up to 10:1 respectively.

After mixing the plant with the solvent, a concentration of approximately 0.3% bulbocapnine and tetrahydropalmatine and total alkaloid content of approximately 1.5% was notedly expected. After the purification and isolation steps of the method, the alkaloid content in this embodiment will have a minimum concentration of 18:1. Other non-primary target molecules including protopine, α-allocryptopine, tetrahydrocolumbamine, coptisine, palmatine, berberine, dehydrocorydaline, tetrahydroberberine, corydaline and tetrahydrocoptisine have a minimum concentration range in this embodiment of from 2:1, 5:1, 8:1, to up to 10:1, respectively, after purification.

The extraction process consistently demonstrates higher yields. For instance, the experiment was run four times four and run through chromatography as discussed herein. The same conditions were used, and the below table provides the output of bulbocapnine, THP, and other target molecules detected in the elution and isolation step for each of the four runs.

Figure 2:
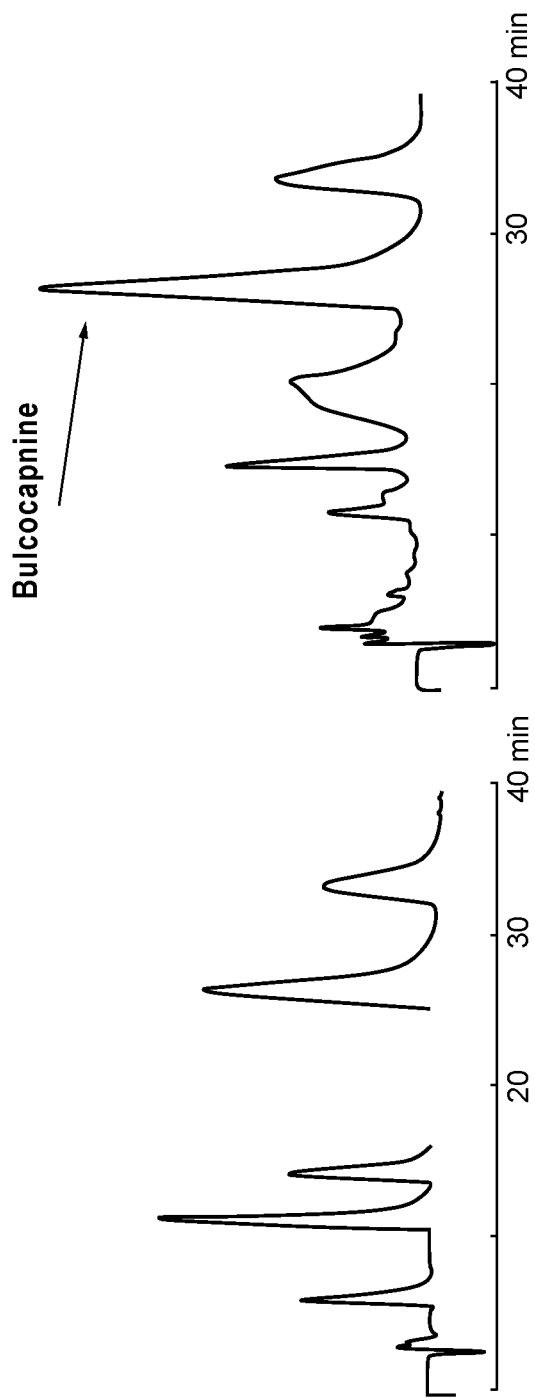
FIG. 2 illustrates a mass spectrometry of a *C. yanhusuo* sample comprising bulbocapnine.
Figure 3:
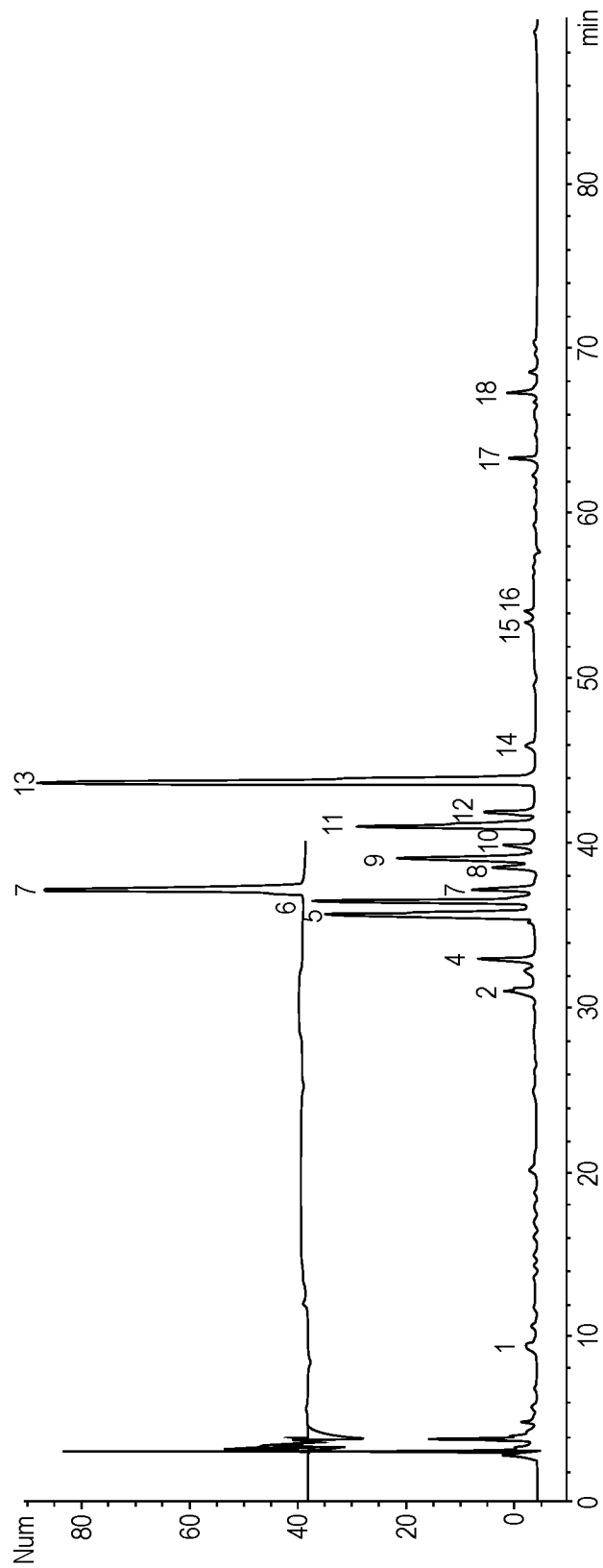
FIG. 3 illustrates a mass spectrometry of a further *C. yanhusuo* sample.
Figure 4:
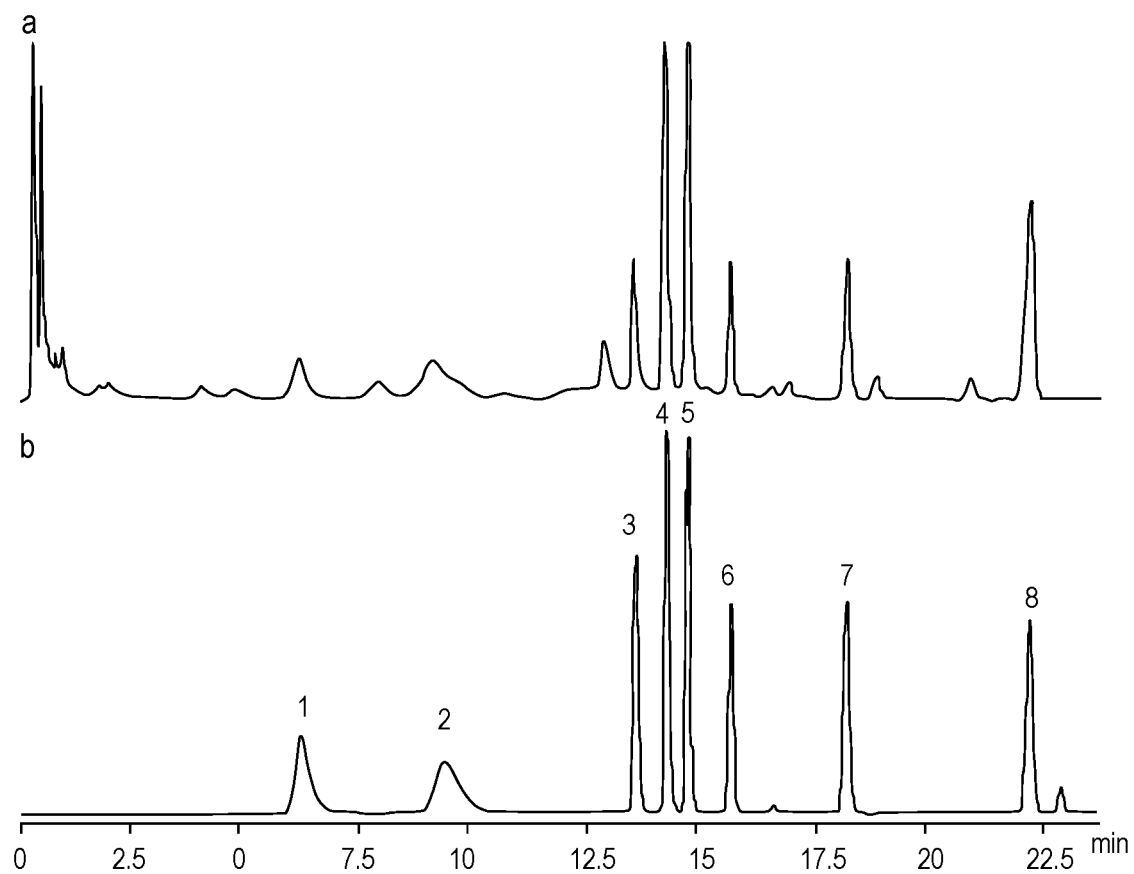
FIG. 4 illustrates a mass spectrometry of a *C. yanhusuo* sample before and after enhanced concentration of select target molecules through the inventive process disclosed herein.

FIG. 2 shows an illustrative chromatogram of C. yanhusuo comprising bulbocapnine.

Embodiments of the concentration of target molecules are 18:1, 25:1, or 40:1. These are then resuspended in raw crude extract at a 1:1 concentration with the target molecules. Unexpectedly, this does not increase the concentration of the raw crude extract, but rather, it spikes or unexpectedly selects for certain target molecules within the combination while at the same time isolates additional molecules in the extract as well which were not expected or potentially were unknown. This provides the benefit of the variety of molecules both known and unknown within the crude extract as well as the benefit of including the added concentrated, purified target molecules.

Experimental results also show that the bulk extraction of C. yanhusuo is an effective extraction process for retrieving alkaloids contained in the C. yanhusuo plant which possess significant bioactivity include: bulbocapnine, tetrahydropalmatine, protopine, α-allocryptopine, tetrahydrocolumbamine, coptisine, palmatine, berberine, dehydrocorydaline, tetrahydroberberine, corydaline, and tetrahydrocoptisine. As such, the extraction process and methodologies are capable of providing consistent results, through many trials and routine experimentation in the art.

Providing the concentrated, stabilized target molecules at an effective concentration of 2:1 or more in order to achieve desired biological activities unexpectedly and advantageously produced the unknown heightened "entourage effect" of countless other phytonutrients in the plant that were not extracted, and thus provides a "whole-herb" extract delivery for medicinal and commercial use. This heightened "entourage effect" activity through the extraction method of the C. yanhusuo plant also provides unrealized insight in relation to how phytochemicals and cannabinoids are metabolized by the body through the endocannabinoid system. As a result of the higher yields of the alkaloids in the C. yanhusuo plant and the heightened entourage effect, further advancements with mixtures of these alkaloid products with additional phytonutrients, phytomaterials, and phytochemicals such as cannabinoids themselves can be envisioned for enhanced synergistic effects. Medicinal uses and commercial uses are both envisioned.

Some medicinal uses may include, but are not limited to, compositions for treatment of psychological disorders ranging from depression to anxiety. The resulting compositional output of the present method may be used to treat disorders in the form of a sleep aid, pain relief, performance enhancer, premenstrual syndrome, and eating disorders.

Various delivery vehicles can be used, as discussed above, and the choice of the same will depend on various factors such as, but not limited to, the desired result or ease of manipulation or even the speed of delivery or efficacy, and the concentration of the final composition of the present method could be dictated by the desired effect, the subject, what is being treated, a combination of any of the same and other factors.

While certain embodiments of the methods herein have been described in detail with reference to the accompanying figures, it should be apparent that modifications and variations thereto are possible, all of which fall within the true spirit and scope of the invention. The invention also includes all of the steps, features, compositions and compounds referred to or indicated in this specification, individually or collectively, and any and all combinations of any two or more of said steps or features.

As such, those skilled in the art will appreciate that the conception, upon which this disclosure is based may readily be utilized as a basis for other compositions, formulations, methods and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of the application, which is measured by the claims, nor is it intended to be limiting as to the scope of the invention in any way.

These together with other aspects of the invention, along with the various features of novelty that characterize the invention, are pointed out with particularity in the claims annexed to and forming a part of this disclosure. For a better understanding of the invention, its operating advantages and the specific aspects attained by its uses, reference should be had to the accompanying figures and description matter in which there are illustrated preferred embodiments of the invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method of extracting a *Corydalis yanhusuo* (*C. yanhusuo*) plant comprising the steps of:
    harvesting and drying the *C. yanhusuo* plant;
    extracting alkaloids comprising bulbocapnine and/or tetrahydropalmatine from the *C. yanhusuo* plant in a solvent;
    filtering the solvent-*C. yanhusuo* plant mixture to remove the solvent and extracted alkaloids from a spent *C. yanhusuo* plant matter;
    drying the spent *C. yanhusuo* plant matter;
    purifying and separating the extracted alkaloids from the solvent; and
    mixing the extracted alkaloids back into the dried spent *C. yanhusuo* plant matter.

2. The method according to claim 1, wherein the *C. yanhusuo* plant has a total alkaloid content of about 3%, of which, about 97% are a combination of bulbocapnine and tetrahydropalmatine.

3. The method according to claim 1, wherein the solvent is selected from the group consisting of ethanol, methanol, hydroalcohol, acetone, acetonitrile, hexane, heptane, hexane, chloroform, dichloromethane, water, and mixtures thereof.

4. The method according to claim 3, wherein the solvent is ethanol.

5. The method according to claim 1, wherein the removal of the solvent is by a process selected from the group consisting of distillation, open-dish evaporation, reduced-pressure evaporation, rotary evaporation, vacuum, lyophilization, or a combination of methods thereof.

6. The method according to claim 5, wherein the removal of the solvent is by rotary evaporation.

7. The method according to claim 1, wherein the purification and separation of the alkaloids is carried out by passing the solvent and extracted alkaloids over or through a process selected from the group consisting of column chromatography comprising a reverse stationary phase, a normal stationary phase or combination thereof, ion-exchange chromatography, gel-permeation (molecular sieve) chromatography, affinity chromatography, paper chromatography, thin-layer chromatography, gas chromatography, dye-ligand chromatography, hydrophobic interaction chromatography, pseudoaffinity chromatography, and high-pressure liquid chromatography (HPLC).

8. The method according to claim 1, wherein the method further comprises
    adding cannabidiols (CBD) to the *C. yanhusuo* plant and the solvent during extraction.

9. The method according to claim 8, wherein the cannabidiols source is selected from the group consisting of hemp plant, crude hemp oil, kief, nabiximol, epidiolex, and combinations thereof.

10. The method according to claim 9, wherein the cannabidiols source is crude hemp oil.

11. The method according to claim 1, wherein the method further comprises
    adding cannabidiols (CBD) to the mixture of the purified alkaloids and the dried spent *C. yanhusuo* plant matter.

12. The method according to claim 11, wherein the cannabidiols source is selected from the group consisting of hemp plant, crude hemp oil, kief, nabiximol, epidiolex, and combinations thereof.

13. The method according to claim 12, wherein the cannabidiol source is crude hemp oil.

14. The method according to claim 1, wherein the method further comprises
    solubilizing the mixture of the purified alkaloids and the dried spent *C. yanhusuo* plant matter in a second solvent.

15. The method according to claim 14, wherein the second solvent is selected from the group consisting of ethanol, methanol, hydroalcohol, acetone, acetonitrile, hexane, heptane, hexane, chloroform, dichloromethane, water, and mixtures thereof.

16. The method of claim 14, further comprising the step of infusing into a vaporizing liquid the mixture of the purified alkaloids and the dried spent *C. yanhusuo* plant matter.

17. The method of claim 14, further comprising the step of infusing into a medicinal composition the mixture of the purified alkaloids and the dried spent *C. yanhusuo* plant matter.

18. The method of claim 14, further comprising the step of infusing into a kief composition the mixture of the purified alkaloids and the dried spent *C. yanhusuo* plant matter.

19. The method of claim 14, further comprising the step of infusing into a rolling paper the mixture of the purified alkaloids and the dried spent *C. yanhusuo* plant matter.

20. The method of claim 14, further comprising the step of infusing into a smoking filter a mixture of the purified alkaloids and dried spent *C. yanhusuo* plant matter.

* * * * *